(12) United States Patent
Clancy et al.

(10) Patent No.: US 6,974,674 B1
(45) Date of Patent: Dec. 13, 2005

(54) PREDISPOSITION TO INFECTION ASSOCIATED WITH INTENSE EXERCISE OR OTHER STRESS

(75) Inventors: Robert Llewellyn Clancy, Newcastle (AU); Maree Gleeson, Merewether (AU)

(73) Assignee: The University of Newcastle Research Associates Limited, Callahan (AU)

( * ) Notice: Subject to any disclaimer, the term of this patent is extended or adjusted under 35 U.S.C. 154(b) by 0 days.

(21) Appl. No.: 09/913,297

(22) PCT Filed: Feb. 10, 2000

(86) PCT No.: PCT/AU00/00085

§ 371 (c)(1),
(2), (4) Date: Dec. 11, 2001

(87) PCT Pub. No.: WO00/48001

PCT Pub. Date: Aug. 17, 2000

(30) Foreign Application Priority Data

Feb. 10, 1999 (AU) .................................... PP8603

(51) Int. Cl.$^7$ ............................................ G01N 33/53
(52) U.S. Cl. ....................... 435/7.1; 435/7.92; 436/513
(58) Field of Search ............................... 435/7.1, 7.92; 436/513

(56) References Cited

OTHER PUBLICATIONS

Gleeson, M., et al., "Salivary IgA subclasses and infection risk in elite swimmers", Immunology and Cell Biology, 77:351-355 (1999).

Gleeson, M., et al., "Salivary IgA levels and infection risk in elite swimmers", Medicine & Science in Sports & Exercise, 31(1) 67-73 (Jan. 1999).

Pyne, D.B. et al., "Effects of Intensive Exercise Training on Immunity in Athletes", Int. J. Sports Med., 19 (supp 3) 183-194 (Jul. 1998).

Tharp, G. D. et al, "Reduction of saliva immunoglobulin levels by swim training", Eur. J. Appl. Physiol., 60:61-64 (1990).

McKinnon, L. T. et al., "Mucosal (Secretory) Immune System Responses to Exercise of Varying Intensity and During Overtraining", Int. J. Sports Med., 15:197-183 (1994).

Warner, R. H. et al., "Salivary SigA and SigA 1 in Coeliac Disease, Inflammatory Bowel Disease and Controls", ltr. J. Med. Sc., 168 (1):33-35 (Jan. Feb. Mar. 1999)11111111.

Primary Examiner—Patrick J. Nolan
(74) Attorney, Agent, or Firm—Fish & Neave IP Group Ropes & Gray LLP (57) ABSTRACT

The present invention is concerned with methods for determining predisposition to infection in a subject exposed to stressors. In particular the present invention is concerned with methods of assessing the risk of susceptibility to infection in a subject by monitoring the levels of IgA and IgA1.

42 Claims, 6 Drawing Sheets

Pan Pacs – Salivary IgA/Infection Study
Figure 3 – Infection Data Time Points

PREDISPOSITION TO INFECTION ASSOCIATED WITH INTENSE EXERCISE OR OTHER STRESS

This application is the U.S. national phase application of, and claims priority from, PCT/AU00/00085, international filing date 10 Feb. 2000, and from Australia PP 8603, filed 10 Feb. 1999, the specifications of which are incorporated herein by reference.

TECHNICAL FIELD

The present invention is concerned with methods for determining predisposition to infection in a subject exposed to stressors. In particular the present invention is concerned with methods of assessing the risk of susceptibility to infection in a subject by monitoring levels of IgA and IgA1.

BACKGROUND ART

Secretary IgA (SIgA) is the predominate form of antibody that mediates specific immunological defence at mucosal surfaces (1). Protection is afforded by several recognised mechanisms; interfering with microbial adherence to mucosal surfaces, inhibiting penetration of antigens across the epithelial membrane, complexing with antigens at the basolateral surface of the mucosal epithelium to facilitate elimination by exocytosis into the mucosal lumen, and salvage mechanisms at intracellular and interstitial levels (2). In humans, immunoglobulin A (IgA) occurs as two subclasses that differs in amino acid sequences and glycosylation of the alpha heavy chain (3). IgA1 predominates (approximately 90%) in serum, whereas IgA2 predominates in most mucosal secretions (4). The proportions of the two subclasses vary between mucosal sites due to differences in the distribution of immunoglobulin producing immunocytes (1,5–6). Saliva contains approximately 60% IgA1 in normal adults (4,7–8).

Research into salivary IgA levels in exercising populations has received considerable attention due to reports of a high prevalence of respiratory infections in elite athletes (9–12). The associations between changes in salivary IgA concentrations with exercise are complex and depend on the intensity, duration and periodicity of training and degree of fitness of the athlete (13–14). Salivary IgA concentrations have been shown to be reduced after intense exercise in the elite athletes training in a variety of endurance sports (14–19). The only report of the influence of exercise on IgA subclasses has been a study of maximal exercise on total IgA and IgA subclasses in human breastmilk (20). In the breastmilk, total IgA and IgA1 but not IgA2 concentrations were decreased after exhaustive exercise, with recovery to baseline levels within 60 minutes (20).

Recently it was reported that low concentrations of IgA in saliva of elite swimmers and a moderately exercising group were associated with an increased risk of respiratory infection (16). Longitudinal studies with elite swimmers have also shown a significant decline in salivary IgA concentrations over a 7-month training season (15–16). However, not all swimmers undertaking the training program were susceptible to infection.

There remains a need for a suitable and timely test to predict susceptibility to infection in subjects exposed to physical or other stress.

It is an object of the present invention to overcome or ameliorate at least some of the disadvantages of the prior art, or to provide a useful alternative.

SUMMARY OF THE INVENTION

As mentioned previously, IgA includes two subclasses, IgA1 and IgA2. It was unexpectedly found that, of these two subclasses, IgA1 levels in a subject exposed to a stressor are the better indicator of susceptibility to infection. It was also unexpectedly found that the best predictive results using total IgA as an indicator susceptibility to infection are obtained when IgA is measured in the early training phase. Further, it was also found that if the decrease in IgA levels which occurs after exposure to a stressor is not recovered rapidly, prolonged reduction in IgA level results. As mentioned above, reduced IgA levels are an indicator of susceptibility to infection.

According to a first aspect, the invention provides a method for assessing potential susceptibility to infection in a subject exposed to a stressor or stressors including:
  (a) determination of the subject's immunoglobulin A (IgA) level in a training phase; and
  (b) prediction of the subject's susceptibility to infection by comparison of the training phase IgA level with a predetermined threshold value.

According to a second aspect, the invention provides a method for assessing potential susceptibility to infection in a subject exposed to a stressor or stressors including:
  (a) determination of the subject's immunoglobulin A1 (IgA1) level; and
  (b) prediction of the subject's susceptibility to infection by comparison of the IgA1 level with a predetermined threshold value.

According to a third aspect, the invention provides a method for monitoring a subject's progress following intervention therapy including:
  (a) determination of the subject's IgA1 level; and
  (b) monitoring the subject's progress by comparison of said IgA1 level with a predetermined threshold value.

According to a fourth aspect, the invention provides a method for assessing the impact of a stressor or stressors on a subject's performance and/or fatigue levels, as defined herein, including:
  (a) determination of the subject's salivary IgA1 level; and
  (b) assessing the impact of the stressor or stressors on the subject's performance and/or fatigue levels by comparison of said IgA1 level with a predetermined threshold value.

According to a fifth aspect, the invention provides a method for assessing potential susceptibility to respiratory infection in an elite swimmer, including:
  (a) determining the swimmer's salivary immunoglobulin A (IgA) level in early training phase; and
  (b) predicting the swimmer's potential susceptibility to respiratory infection by comparison of the early training phase IgA level with a predetermined threshold value.

According to a sixth aspect, the invention provides a method for assessing potential susceptibility to respiratory infection in an elite swimmer, including:
  (a) determining the swimmer's salivary immunoglobulin A1 (IgA1) level in early training phase; and
  (b) predicting the swimmer's potential susceptibility to respiratory infection by comparison of the early training phase IgA1 level with a predetermined threshold value.

According to a seventh aspect, the invention provides a method for assessing a subject's potential susceptibility to infection including:

(a) determining the subject's immunoglobulin A (IgA) level after exposure to a stressor or stressors;
(b) allowing a recovery period as herein defined;
(c) determining the subject's IgA level after the recovery period;
(d) predicting the subject's potential susceptibility to infection by comparison of the IgA level at step (a) above with the IgA level at step (c) above.

According to an eighth aspect, the invention provides a method for assessing a subject's potential susceptibility to infection including:
(a) determining the subject's immunoglobulin A1 (IgA1) level after exposure to a stressor or stressors;
(b) allowing a recovery period as herein defined;
(c) determining the subject's IgA1 level after the recovery period;
(d) predicting the subject's potential susceptibility to infection by comparison of the IgA1 level at step (a) above with the IgA1 level at step (c) above.

Preferably, the immunoglobulin level is determined in early training phase.

Preferably, the infection is a mucosal infection and most preferably, the infection is a respiratory infection.

Preferably, the threshold value is a normal population threshold value. However, in certain instances it may be more appropriate to use an internal personal threshold value.

Preferably, the immunoglobulin is secretory immunoglobulin. Preferably, the secretory immunoglobulin is salivary immunoglobulin. Preferably, the salivary immunoglobulin is from a sample of whole unstimulated saliva and most preferably the subject is not fasting when the saliva is collected.

Preferably, the subject is an athlete. Preferably, the athlete is an elite swimmer.

Preferably, the stressor is known to influence the efficacy of the immune system.

Preferably, the subject is exposed to a physical and/or psychological stressor. Preferably, the physical and/or psychological stressor is long-term physical training or over-training.

Preferably, the immunoglobulin level is determined by radial immunodiffusion or ELISA. Preferably, the immunoglobulin level is determined by a rapid near-subject assay. Preferably, the saliva is analysed for the immunoglobulin content in situ by contacting an assay device or system with the saliva of a subject. Preferably, the assay is a self-test performed by the subject.

In the context of the present invention, the word "stressor" includes within its meaning but is not limited to physical, physiological, psychological and nutritional stressors which include fatigue.

In the context of the present invention, the word "performance" includes within its meaning performance in relation to other subjects, or performance in relation to personal performance level. Similarly, the term "fatigue" includes within its meaning fatigue in relation to other subjects or fatigue in relation to personal fatigue level.

In the context of the present invention, the word "pre-season" will be understood by those skilled in the art to mean "prior to a return training".

In the context of the present invention, the words "early training phase" will be understood by those skilled in the art to mean "the first microcycle of training after a rest period".

In the context of the present invention, the words "late training phase" will be understood by those skilled in the art to mean "the microcycle of training prior to competition".

While the present invention has been exemplified by examples relating to athletes exposed to a physical stressor, it will be clear to those skilled in the art that similar assessment of susceptibility to infection will apply to other stressful professions and activities eg medical and nursing professions, business and professional travellers, where the stressors may be physical and/or non-physical stressors including physiological and psychological stressors and the like. Further, the present invention will also be applicable to patients exposed to the stress of intervention therapy.

In the context of the present invention, the term "intervention therapy" includes invasive/aggressive medical treatments/procedures including surgical and non-surgical interventions and the like.

In the context of the present invention the term "recovery period" includes a period of rest after exposure to a stressor or stressors. The appropriate length of time for recovery will be determined by the skilled addressee and will vary with the type of stressor and the subject exposed to stress.

Although the present invention has been described predominantly in the context of susceptibility to infection, including reactivation of latent infection, it will be understood by those skilled in the art that the same principles can be applied to assessing impaired performance and fatigue.

DESCRIPTION OF THE PREFERRED EMBODIMENT

The concentration of IgA1 in a sample taken from a subject to be tested is determined by radial immunodiffusion (RID) using commercially prepared low-level RID plates and calibrators. ELISA or other technologies applicable to rapid near-subject testing. The present results show that depressed concentrations of IgA1 are particularly associated with a higher risk of infection.

First Study

EXAMPLE 1

Subjects and Study Design

Whole unstimulated saliva was collected from 25 elite swimmers (16 males, 9 females) during the early (April to June) and late (August to October) phases of a 7-month training program (15). The mean time between sample collections for individual athletes was 4 months. The saliva samples were collected prior to the first exercise session on the day of collection and at least 18 hours after the previous exercise session The swimmers aged 16–24 years were undertaking 20–25 hours of pool training and 5 hours of dry-land training per week. Every episode of respiratory infection was recorded during the study and physician-verified (16). The study was conducted with the informed consent of the Australian Institute of Sport (AIS) Swimming Team and had ethics clearance from the Australian Sports Commission.

EXAMPLE 2

Determination of Total IgA, IgA1 and IgA2

The concentration of total IgA in whole unstimulated saliva was measured by electroimmuno diffusion (21). The concentrations of IgA1 and IgA2 were determined by radial immunodiffusion (RID) using one batch number of commercially prepared low level RID plates and calibrators. (The Binding Site, Birmingham, UK). The detection limit of the assays was 4.0 mg/L for total IgA, 8.3 mg/L for IgA1 and 7.5 mg/L for IgA2. The between run CVs were 3.5% for total IgA, 4.1% for IgA1 and 3.0% IgA2.

EXAMPLE 3

Statistical Analysis

For the purposes of this study the athletes were classified as either having no infections ('healthy') or at least one infection episode during the study period. The Wilcoxon signed rank test for paired data was used to compare ratio values between 'healthy' athletes and athletes who had at least one infection during the study period. Spearman's correlation coefficients were used to determine the association between the number of infections and the concentrations of total IgA, IgA1, IgA2, and the ratio of IgA1:IgA2 in the early and late training phase saliva samples. The Mann-Witney Rank Sum Test was used to compare differences between genders for the percentage of nil-detected values of IgA2. A p-value of <0.05 was considered significant.

EXAMPLE 4

Total IgA, IgA1 and IgA2 Concentrations

Figure 1:
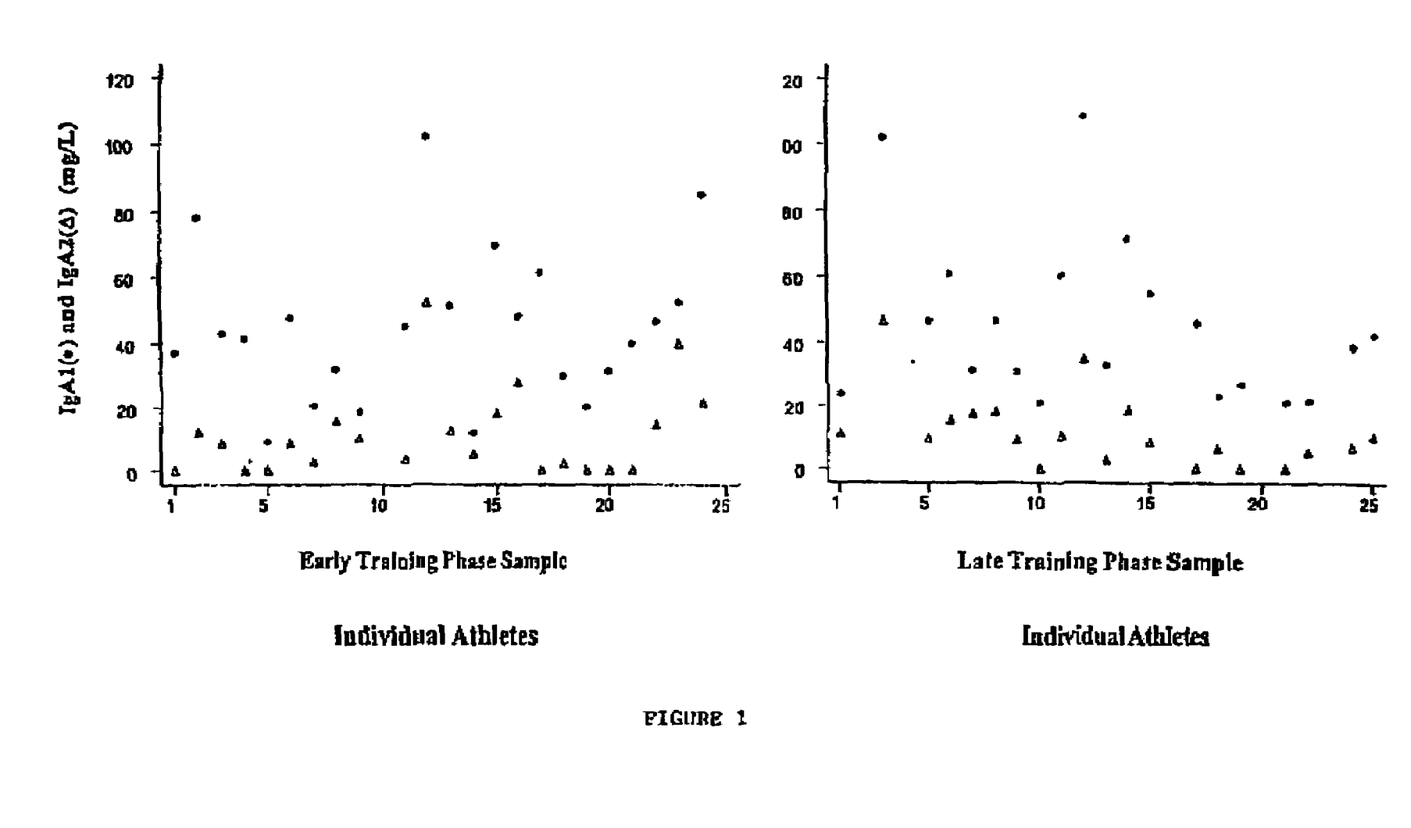
FIG. 1 Concentrations (mg/L) of IgA1 (*) and IgA2 ($\Delta$) in saliva samples collected from 25 elite swimmers during early and late phases of a 7-month training season.

The median concentrations of total IgA, IgA1, IgA2 or the ratio of IgA1:IgA2 were not statistically significantly different between saliva samples collected in the early and late phases of the training program (Table 1). On average IgA1 represented 80% of the total IgA saliva collected in both the early and late phases of the season (Table 1, FIG. 1). There were 11 samples with IgA2 concentrations below the detection level of the RID assay; 7 of the early phase samples and 4 of the late phase sample collections. There were no significant differences between gender for the median concentrations of IgA2 or the proportions with nil detected values for IgA2 in either the early or late season samples (Table 2).

TABLE 1

The Median (95% Confidence interval (CI) of the median) and range of salivary IgA concentrations (mg/L) for total IgA, IgA1 and IgA2 in samples collected from elite swimmers in early and late phases of a 7-month training season. The ratio of IgA1 to IgA2 concentrations is presented for all samples with detectable concentrations. The p-value represents the significance of differences between the concentrations and ratios in early and late training phase samples.

| Salivary IgA | n | Early Training Phase Sample | | | n | Late Training Phase Sample | | | Significance p-value |
|---|---|---|---|---|---|---|---|---|---|
| | | Median (95% CI) | | Range | | Median (95% CI) | | Range | |
| Total IgA | 23 | 43.0 (28.5–59.5) | | 14–96 | 20 | 45.5 (33.8–55.0) | | 25–80 | 0.68 |
| IgA1 | 23 | 43.0 (31.6–50.7) | | 9–102 | 20 | 40.8 (27.5–54.1) | | 21–109 | 0.99 |
| IgA2 | 23 | 8.5 (0.5–14.0) | | 0–53 | 20 | 9.3 (5.1–15.0) | | 0–47 | 0.64 |
| IgA1:IgA2 | 16 | 4.0 (2.0–6.0) | | 1–15 | 16 | 3.9 (2.9–5.4) | | 2–13 | 0.79 |

TABLE 2

The number and proportion of male and female swimmers with IgA2 concentrations below the detection limits in saliva samples collected in the early and late phases of a 7-month training season. The p-value represents the significance of differences between genders in each phase of training.

| Training Phase | Male Swimmers | | | Female Swimmers | | | Significance p-value |
|---|---|---|---|---|---|---|---|
| | Total IgA (n) | Low IgA2 (n) | PND* (%) | Total IgA (n) | Low IgA2 (n) | PND* (%) | |
| Early Sample | 14 | 4 | 29 | 9 | 3 | 33 | 0.48 |
| Late Sample | 13 | 3 | 23 | 7 | 1 | 14 | 0.38 |

*Proportion Not Detected

EXAMPLE 5

Infections

Figure 2:
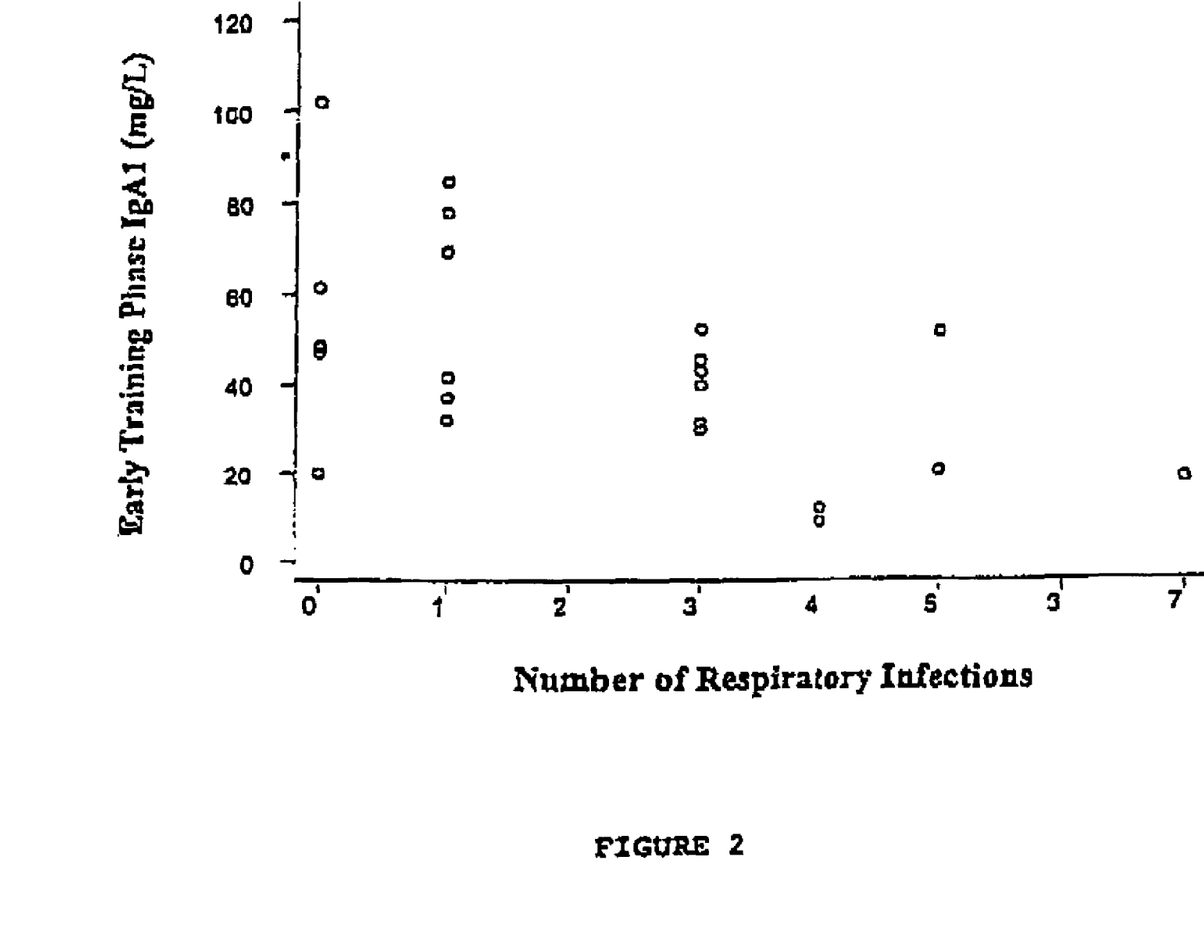
FIG. 2 Concentrations of IgA1 (mg/L) in the early phase of training for each swimmer and the number of infection episodes recorded during a 7-month training season.

Seven swimmers (5 males, 2 females) has no episodes of respiratory infection during the 7 month study. The number of infection episodes in the other 18 swimmers ranged from one to seven (FIG. 2). The correlations between the number of infections and the concentrations of total IgA, IgA1 and IgA2 (Table 3) showed a statistically significant association between the early season salivary IgA1 concentration and the number of infection episodes in each athlete (FIG. 2). The correlation between the early season salivary IgA1 and the number of infections remained significant (p=0.04) even after removing the athlete with the high number of infections (n=7) from the calculation. There were no statistically significant correlations for other variables (Table 3). Although the ratio of IgA1:IgA2 tended to be lower in swimmers who had no infection episodes during the 7-month training season (Table 4) there were no statistically significant differences in the early or late phase samples collected from athletes who had no infections compared to those who had at least one infection episode.

TABLE 3

The Spearman's correlation coefficient (Rho) and significance of the correlations between the number of infections for each swimmer and the concentrations or ratios of total IgA, IgA1 and IgA2 in early and late training phase saliva collections.

|  | Early Training Phase Sample | | Late Training Phase Sample | |
| --- | --- | --- | --- | --- |
| Salivary IgA | Spearman's Rho | p-value | Spearman's Rho | p-value |
| Total IgA | −0.31 | 0.16 | −0.40 | 0.10 |
| IgA1 | −0.51 | 0.01 | −0.08 | 0.76 |
| IgA2 | −0.18 | 0.41 | 0.15 | 0.56 |
| IgA1:IgA2 | 0.20 | 0.46 | −0.01 | 0.98 |

TABLE 4

The median and range of ratios of IgA1:IgA2 concentrations in saliva samples collected during early and late phases of training in swimmers with no infections compared with swimmers who had at least one infection during a 7-month training season. The p-value represents the differences between the 'healthy' and infection-prone swimmers.

|  | No Infection Episodes IgA1:IgA2 Ratio | | | At Least One Infection IgA1:IgA2 Ratio | | | Significance |
| --- | --- | --- | --- | --- | --- | --- | --- |
| Training | n | Median | Range | n | Median | Range | p-value |
| Early Sample | 4 | 2.6 | 2–6 | 12 | 4.1 | 1–15 | 0.25 |
| Late Sample | 3 | 3.9 | 3–4 | 13 | 3.9 | 2–13 | 0.84 |
| Sample Total | 7 | 3.2 | 2–6 | 25 | 4.1 | 1–15 | 0.24 |

The results of this study of elite swimmers indicate that low concentrations of IgA1 below 25 mg/L (FIG. 2) in saliva collected early in a 7-month training season were selectively associated with a higher risk of respiratory tract infection episodes during the season. A previous study of respiratory infections in elite swimmers revealed that pre-season concentrations of total IgA below 35 mg/L were associated with high numbers of infection episodes (16). In the current study the saliva samples were collected early in the training season but not prior to the commencement of the training season.

IgA1 represented approximately 80% of the total IgA concentration in this cohort of elite swimmers. In studies of normal non-exercising adults the proportion of IgA1 in saliva is approximately 60% (4,7–8). IgA1 antibodies are primarily produced in response to protein antigens while IgA2 antibodies are induced by carbohydrates and lipid-containing antigens (1). The fact that IgA1 proteases produced by most mucosal pathogens can degrade IgA1 antibodies, while IgA2 antibodies are protected (1) is on importance when considering resistance to infections at mucosal surfaces. As IgA1 is more susceptible to the proteases produced by mucosal pathogens (1), the higher proportion of IgA1 and the occasional non-detectable levels of IgA2 in this cohort of elite swimmers may combine to increase their risk of mucosal infections. Despite a small portion of samples having IgA2 concentrations below the assay detection limit there were no associations between IgA2 concentration or the ratios of the subclasses with infection rates.

As many of the elite swimmers in this study had been competing and training for several years, it is possible that the levels of IgA1 in the early training phase saliva collections represent a cumulative effect over the years of training of exercise-induced IgA1 suppression.

Second Study

The Pan Pacs Championships (swimming) were held in Sydney, Australia between 22 Aug. 1999 and 29 Aug. 1999. A further competition was held in Canberra, Australia the following week between 1 Sep. 1999 and 5 Sep. 1999. The swimmers' IgA levels and infection data were collected during the training phase leading up to and during these competitions.

EXAMPLE 6

Definitions

Figure 3:
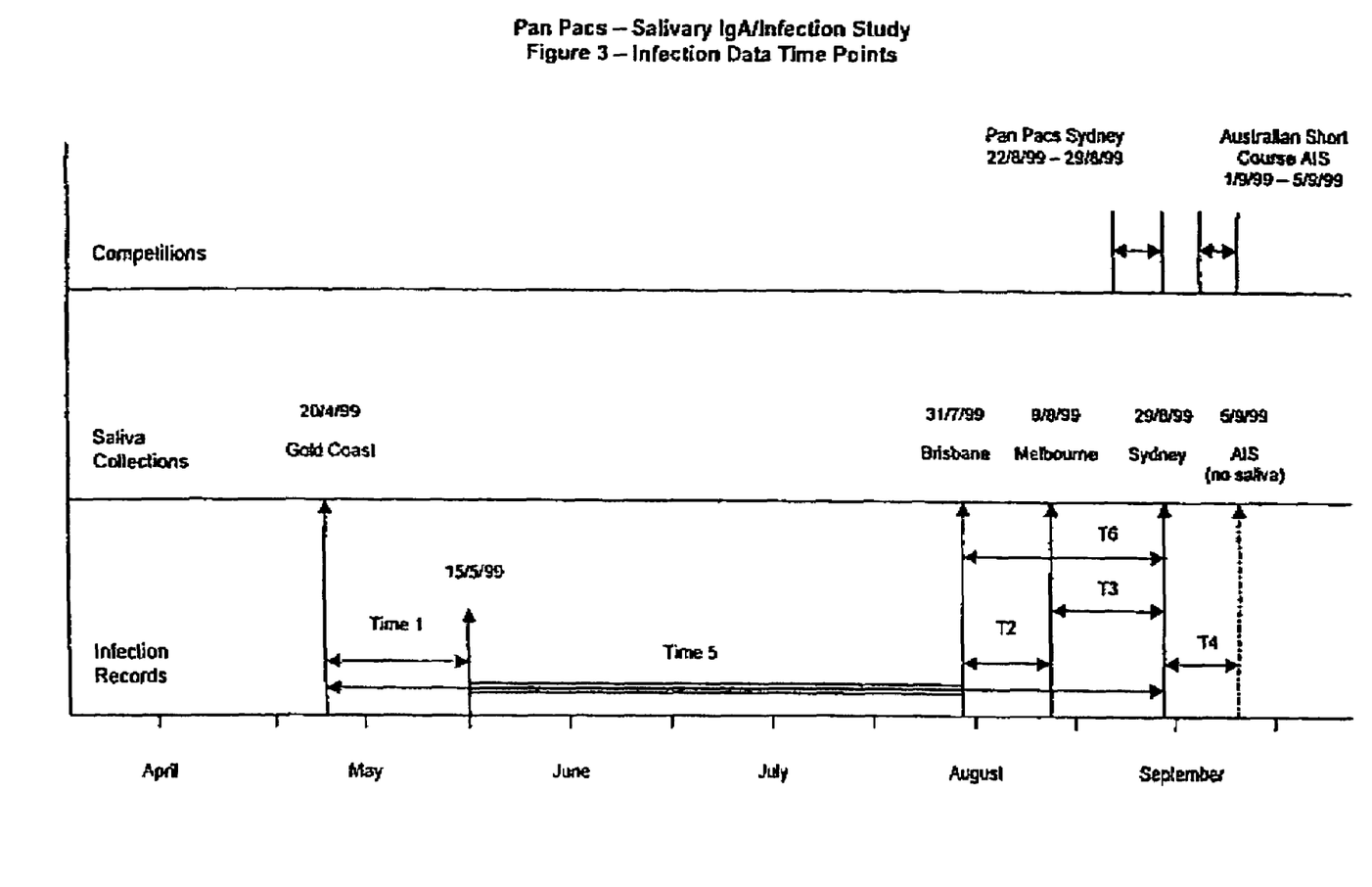
FIG. 3 Infection data time points in the Pan Pacs—Salivary IgA/Infection Study

Infection was defined as yes/no between defined time points of data collection (Table 5) after each saliva collection (FIG. 3).

TABLE 5

| Time | Infection Data Collection Periods |
| --- | --- |
| 1 | 23/4/99–15/9/99 |
| 2 | 31/7/99–8/8/99 |
| 3 | 9/8/99–29/8/99 |
| 4 | 30/8/99–5/9/99 |
| 5 | 23/4/99–30/7/99* |
| 6 | 31/7/99–30/8/99 |

*Note: Infection Logs were not recorded for 10 weeks between 15/5/99 and 30/7/99.

Saliva was collected unstimulated, non-fasting, and pre-exercise on four occasions (Table 6).

TABLE 6

| Training Group | Date of Collection | Subjects |
| --- | --- | --- |
| Gold Coast | 20/4/99 | 42 |
| Brisbane | 31/7/99 | 45 |
| Melbourne | 9/8/99 | 42 |
| Sydney | 29/8/99 | 47 |

TABLE 7

Time 1
Comparison of Salivary immunoglobulin Levels collected on 20/04/99
between Subjects with No infection and Subjects with infection during the
period 23/04/99–15/05/89

|  |  | No Infection | | | Infection | | |
| --- | --- | --- | --- | --- | --- | --- | --- |
|  |  | n | median | range | n | median | range | p-value |
| IgA | All | 42 | 66.7 | (18–175) | 21 | 38.6 | (20–172) | 0.08 |
|  | Swimmers Only | 27 | 63.5 | (18–175) | 16 | 32.7 | (20–172) | 0.03 |
|  | Staff Only | 15 | 69.1 | (20–118) | 5 | 90.8 | (20–134) | 0.48 |
| IgG | All | 42 | 8.0 | (0–44) | 21 | 7.1 | (0–37) | 0.71 |
|  | Swimmers Only | 27 | 8.6 | (0–44) | 16 | 6.3 | (0–37) | 0.95 |
|  | Staff Only | 15 | 7.7 | (2–30) | 5 | 17.9 | (3–24) | 0.36 |
| IgM | All | 42 | 5.0 | (0–36) | 21 | 3.3 | (0–9) | 0.13 |
|  | Swimmers Only | 27 | 5.4 | (0–36) | 16 | 3.1 | (2–9) | 0.14 |
|  | Staff Only | 15 | 3.1 | (1–19) | 5 | 3.5 | (0–4) | 0.46 |
| Albumin | All | 42 | 41.6 | (15–155) | 21 | 50.7 | (8–206) | 0.41 |
|  | Swimmers Only | 27 | 45.8 | (15–155) | 16 | 47.4 | (8–180) | 0.80 |
|  | Staff Only | 15 | 39.6 | (20–125) | 5 | 82.7 | (22–206) | 0.21 |

TABLE 8

Time 2
Comparison of Salivary immunoglobulin Levels collected on 31/07/99
between Subjects with No infection and Subjects with infection during the
period 31/07/99–09/08/99

|  |  | No Infection | | | Infection | | |
| --- | --- | --- | --- | --- | --- | --- | --- |
|  |  | n | median | range | n | median | range | p-value |
| IgA | All | 45 | 45.8 | (15–170) | 10 | 30.0 | (16–104) | 0.07 |
|  | Swimmers Only | 31 | 47.8 | (15–134) | 8 | 30.0 | (17–104) | 0.11 |
|  | Staff Only | 14 | 43.7 | (20–170) | 2 | 34.3 | (15–54) | 0.43 |
| IgG | All | 45 | 7.5 | (0–43) | 10 | 5.4 | (3–17) | 0.39 |
|  | Swimmers Only | 31 | 7.5 | (0–43) | 8 | 7.0 | (3–16) | 0.30 |
|  | Staff Only | 14 | 8.2 | (3–22) | 2 | 11.0 | (5–17) | 0.63 |
| IgM | All | 45 | 2.5 | (0–24) | 10 | 2.3 | (0–6) | 0.35 |
|  | Swimmers Only | 31 | 2.2 | (0–10) | 8 | 2.7 | (0–6) | 0.70 |
|  | Staff Only | 14 | 4.6 | (1–24) | 2 | 1.2 | (1–2) | 0.10 |
| Albumin | All | 45 | 54.4 | (17–126) | 10 | 44.8 | (32–104) | 0.57 |
|  | Swimmers Only | 31 | 48.8 | (17–126) | 8 | 44.8 | (34–78) | 0.83 |
|  | Staff Only | 14 | 73.2 | (27–122) | 2 | 67.8 | (32–104) | 0.75 |

TABLE 9

Time 3
Comparison of Salivary immunoglobulin Levels collected on 09/08/99
between Subjects with No infection and Subjects with infection during the
period 09/08/99–30/08/99

|  |  | No Infection | | | Infection | | |
| --- | --- | --- | --- | --- | --- | --- | --- |
|  |  | n | median | range | n | median | range | p-value |
| IgA | All | 42 | 86.3 | (24–226) | 21 | 76.6 | (15–164) | 0.63 |
|  | Swimmers Only | 27 | 78.0 | (24–164) | 11 | 71.0 | (31–164) | 0.62 |
|  | Staff Only | 15 | 89.0 | (30–226) | 10 | 98.3 | (15–134) | 0.78 |
| IgG | All | 42 | 18.1 | (1–38) | 21 | 14.2 | (5–36) | 0.37 |
|  | Swimmers Only | 27 | 15.4 | (1–38) | 11 | 15.0 | (5–32) | 0.97 |
|  | Staff Only | 15 | 18.8 | (5–32) | 10 | 15.0 | (7–36) | 0.07 |
| IgM | All | 42 | 4.6 | (1–27) | 21 | 3.5 | (1–14) | 0.55 |
|  | Swimmers Only | 27 | 4.2 | (1–16) | 11 | 5.4 | (2–9) | 0.65 |
|  | Staff Only | 15 | 5.6 | (2–27) | 10 | 3.2 | (1–14) | 0.18 |
| Albumin | All | 42 | 63.0 | (0–233) | 21 | 43.6 | (21–116) | 0.11 |
|  | Swimmers Only | 27 | 60.8 | (0–233) | 11 | 50.5 | (26–116) | 0.68 |
|  | Staff Only | 15 | 65.1 | (28–112) | 10 | 39.4 | (21–98) | 0.03 |

TABLE 10

Time 4
Comparison of Salivary immunoglobulin Levels collected on 29/08/99 between Subjects with No infection and Subjects with infection during the period 30/08/99–05/09/99

|  |  | No Infection | | | Infection | | | |
| --- | --- | --- | --- | --- | --- | --- | --- | --- |
|  |  | n | median | range | n | median | range | p-value |
| IgA | All | 47 | 44.1 | (20–148) | 6 | 37.3 | (28–79) | 0.48 |
|  | Swimmers Only | 28 | 44.1 | (20–148) | 4 | 37.3 | (33–79) | 0.65 |
|  | Staff Only | 19 | 44.1 | (26–143) | 2 | 38.9 | (28–50) | 0.55 |
| IgG | All | 44 | 7.2 | (2–28) | 6 | 7.7 | (3–14) | 0.68 |
|  | Swimmers Only | 27 | 5.9 | (2–28) | 4 | 4.6 | (3–11) | 0.38 |
|  | Staff Only | 17 | 9.3 | (3–20) | 2 | 12.0 | (10–14) | 0.69 |
| IgM | All | 47 | 3.8 | (1–22) | 6 | 3.0 | (2–6) | 0.40 |
|  | Swimmers Only | 28 | 4.0 | (1–11) | 4 | 3.0 | (2–4) | 0.12 |
|  | Staff Only | 19 | 3.0 | (1–22) | 2 | 4.3 | (2–6) | 0.76 |
| Albumin | All | 47 | 39.8 | (6–153) | 6 | 29.3 | (15–80) | 0.59 |
|  | Swimmers Only | 28 | 35.0 | (7–153) | 4 | 23.9 | (15–80) | 0.53 |
|  | Staff Only | 19 | 47.4 | (14–140) | 2 | 53.3 | (28–78) | 0.90 |

TABLE 11

Time 5
Comparison of Salivary immunoglobulin Levels collected on 20/04/99 between Subjects with No infection and Subjects with infection during the period 23/04/99–30/08/99

|  |  | No Infection | | | Infection | | | |
| --- | --- | --- | --- | --- | --- | --- | --- | --- |
|  |  | n | median | range | n | median | range | p-value |
| IgA | All | 25 | 68.0 | (20–175) | 38 | 44.0 | (18–172) | 0.03 |
|  | Swimmers Only | 17 | 67.7 | (20–175) | 26 | 39.1 | (18–172) | 0.02 |
|  | Staff Only | 8 | 69.6 | (33–118) | 12 | 68.0 | (20–134) | 0.85 |
| IgG | All | 25 | 9.3 | (0–44) | 38 | 7.0 | (0–37) | 0.78 |
|  | Swimmers Only | 17 | 8.6 | (0–44) | 26 | 6.6 | (0–37) | 0.93 |
|  | Staff Only | 8 | 11.5 | (2–27) | 12 | 7.4 | (2–30) | 0.56 |
| IgM | All | 25 | 5.0 | (0–36) | 38 | 3.4 | (0–9) | 0.20 |
|  | Swimmers Only | 17 | 5.0 | (0–36) | 26 | 3.7 | (2–9) | 0.56 |
|  | Staff Only | 8 | 5.3 | (2–19) | 12 | 3.0 | (0–9) | 0.20 |
| Albumin | All | 25 | 43.5 | (16–155) | 38 | 47.2 | (8–206) | 0.94 |
|  | Swimmers Only | 17 | 37.3 | (16–155) | 26 | 47.2 | (8–180) | 0.84 |
|  | Staff Only | 8 | 50.4 | (25–125) | 12 | 45.0 | (20–206) | 0.59 |

TABLE 12

Time 6
Comparison of Salivary immunoglobulin Levels collected on 31/07/99 between Subjects with No infection and Subjects with infection during the period 31/07/99–30/08/99

|  |  | No Infection | | | Infection | | | |
| --- | --- | --- | --- | --- | --- | --- | --- | --- |
|  |  | n | median | range | n | median | range | p-value |
| IgA | All | 34 | 48.2 | (15–170) | 21 | 36.2 | (15–104) | 0.17 |
|  | Swimmers Only | 24 | 49.0 | (15–134) | 15 | 36.2 | (17–104) | 0.23 |
|  | Staff Only | 10 | 47.1 | (20–170) | 6 | 38.9 | (15–100) | 0.59 |
| IgG | All | 34 | 7.8 | (0–43) | 21 | 5.7 | (2–21) | 0.33 |
|  | Swimmers Only | 24 | 7.2 | (0–43) | 15 | 5.7 | (2–21) | 0.54 |
|  | Staff Only | 10 | 10.8 | (3–22) | 6 | 5.5 | (4–17) | 0.45 |
| IgM | All | 34 | 2.5 | (0–24) | 21 | 2.6 | (0–8) | 0.77 |
|  | Swimmers Only | 24 | 2.1 | (0–10) | 15 | 2.6 | (0–8) | 0.10 |
|  | Staff Only | 10 | 4.6 | (1–24) | 6 | 2.4 | (1–6) | 0.17 |
| Albumin | All | 34 | 55.7 | (17–126) | 21 | 44.6 | (17–124) | 0.47 |
|  | Swimmers Only | 24 | 45.6 | (17–126) | 15 | 45.9 | (17–124) | 0.77 |
|  | Staff Only | 10 | 79.7 | (34–122) | 6 | 38.2 | (27–104) | 0.08 |

The number of subjects in the study varied at each time point (see above) due to unavailability of subjects on the day of saliva collection or exclusion of samples for various reason post analysis or Infection Logs not available.

There were no associations between salivary IgG, IgM or Albumin and infection at any of the time points studied.

There was a trend for swimmers who had an infection to have lower salivary IgA concentrations than those without infections (Tables 7 to 12) and at two time points the concentrations of pre-exercise salivary IgA were statistically significantly lower in swimmers who had an infection (Table 13).

TABLE 13

| Time Period | Saliva Collection | Infection Log Period | Salivary IgA No infection (mg/L) | Salivary IgA infection (mg/L) | p-value |
|---|---|---|---|---|---|
| 1 | 20/4/99 | 23/4/99–15/5/99 | 63.5 (18–175) | 32.7 (20–172) | 0.03 |
| 5 | 20/4/99 | 23/4/99–30/8/99 | 67.7 (20–175) | 39.1 (18–172) | 0.02 |

The results suggest that the concentration of salivary IgA in the early season training camp is the best predictor of later infection(s) during training leading up to a major competition.

Figure 4:
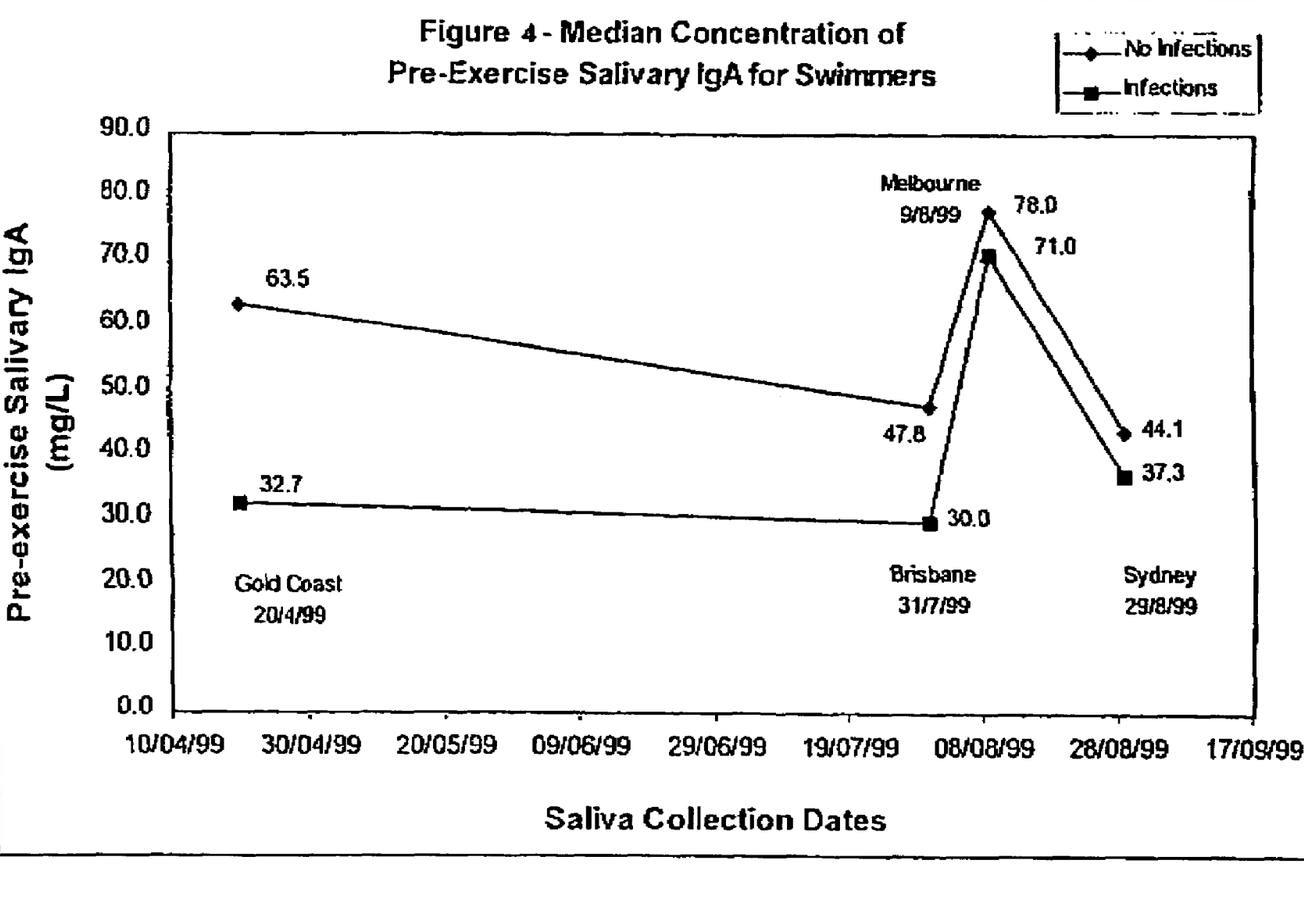
FIG. 4 Median concentration of pre-exercise salivary IgA for swimmers

The median concentration for swimmers reporting no URTIs after each time point decreased over the four month period (63.5 to 44.1 mg/L) while the concentration for swimmers with infections showed little variation (32.7 to 37.3 mg/L) (FIG. 4). This suggests swimmers who are susceptible to infections may already be below a critical threshold level of salivary IgA at the beginning of the season and have little room for further reduction with training.

The increase in salivary IgA in samples collected on 9 Aug. 1999 may be due to the fact that post this saliva collection there was an outbreak of gastrointestinal illness in the training camp, which may reflect mucosal stimulation in the elevated salivary IgA, even prior to the symptoms of gastrointestinal infection.

Third Study

This case study presents data on the application of salivary immunoglobulin monitoring in managing an individual elite kayaker who was prone to recurrent debilitating respiratory illness that interfered with training and preparations for competitions.

EXAMPLE 7

Medical History

The male elite athlete, aged 25 years, had been competing at an international level for 10 years. Five years prior to this study he contracted Epstein-Barr virus (EBV) followed by two episodes of upper respiratory tract illness (URTI). Over the proceeding years the average number of URTI had increased to 5–6 episodes per year and were associated with fatigue. A medical examination excluded all recognised clinical causes of recurrent illness and associated fatigue.

Study Design

Non-fasting, non-stimulated whole mixed saliva samples were collected by a standardised method (27), by the athlete before and again immediately after every exercise session over a 14-day period. An in-house ELISA measured the concentrations of IgA, IgG and IgM and albumin concentrations were measured by rate nephelometry using a Beckman ARRAY analyser (Beckman, Brae, Calif.). The athlete using the PEATS program (24) an adaptation of the method described by Sharp (27), to calculate the intensity of each training session.

Statistical Methods

The Wilcoxon signed rank test for paired data was used to compare pre- and post-exercise session protein values. The Mann-Whitney U test was used to compare values between two selected time periods. Spearmans correlation coefficients were used to assess the association between protein values and day of training and time of day of session.

Salivary Immunoglobulins and Albumin

Figure 5:
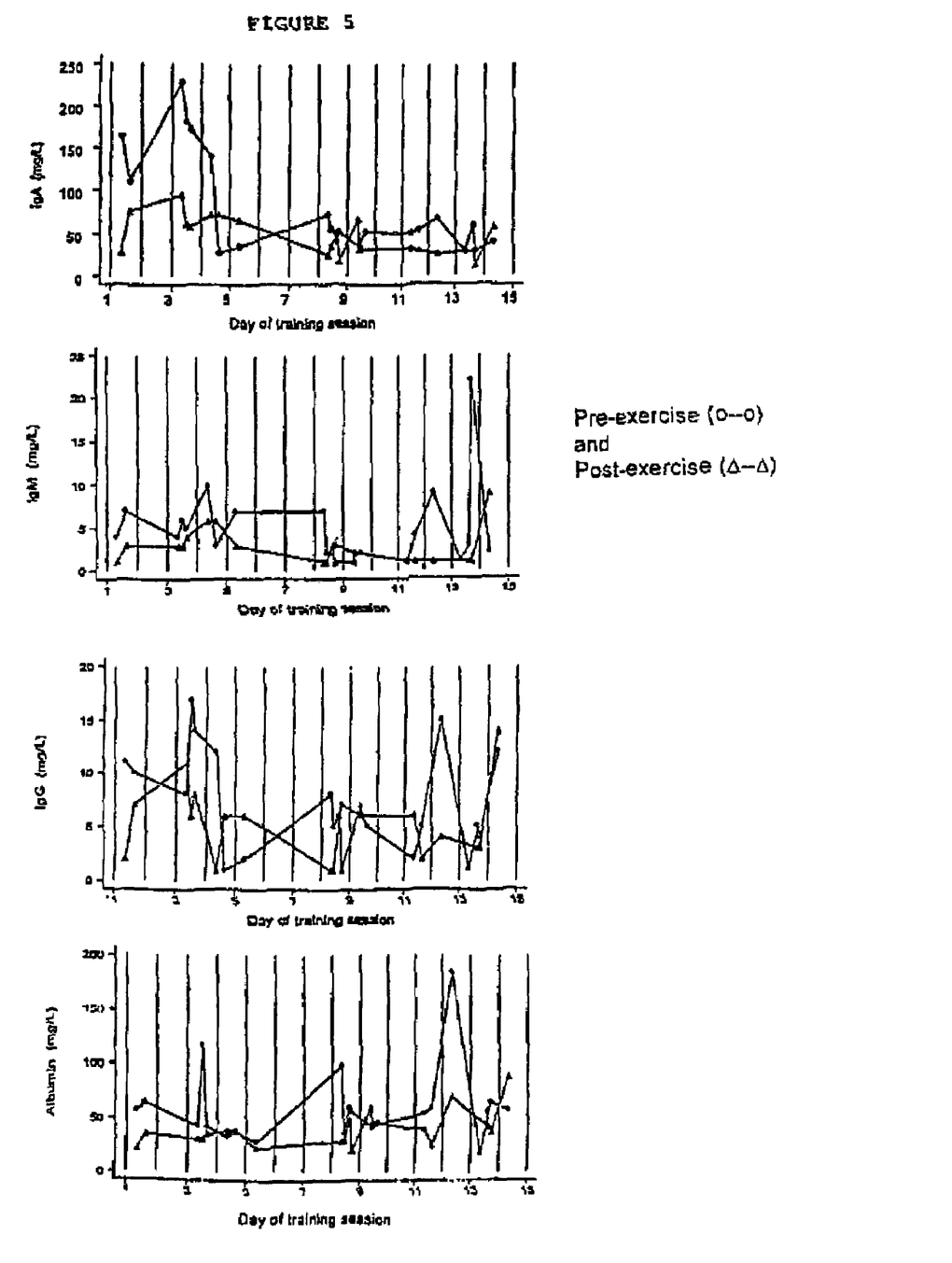
FIG. 5 Pre-exercise (o—o) and post exercise ($\Delta$—$\Delta$) salivary immunoglobulin and albumin concentrations (mg/L) for each training session over the 14 day study period.

The salivary protein concentrations were all on average higher in the pre-exercise session samples compared with the post-exercise session samples (FIG. 5). The median differences were statistically significant (Table 14). The salivary IgA concentrations fell significantly over the two week study (correlation coefficient (rs)=−0.55. P=0.0002) for both the pre-exercise (rs=−0.61, P=0.003) and post-exercise (rs=−0.52, P=0.02) concentrations. There were no significant changes over time for the other salivary proteins. The magnitude of the session change (pre minus post) for salivary IgA concentrations also decreased significantly over time (rs=−0.56, P=0.01), but this was not significant for the other salivary proteins.

The magnitude of the session change for salivary IgA concentrations, but not the other proteins, was positively correlated with the intensity of the exercise session (rs=0.53, P=0.02). The intensity of each exercise session decreased over the two-week study period (rs=−0.45, P=0.03) and was significantly higher (P=0.05) in the first four days (median score≈165, range=80–217) compared to the subsequent ten days of training (median score=110, range=56–185). The concentrations of IgA in both the pre-exercise and post-exercise session samples were significantly higher (P=0.009) for the first four days (median=164 mg/L, range=28–228 mg/L) compared to the last ten days (median=51 mg/L, range=30–72 mg/L). The magnitude of the session change in concentrations for salivary IgA were significantly greater (P=0.02) in the first four days (median=115 mg/L, range=−44–137) compared to the next ten days (median=20 mg/L, range=−30–47 mg/L), being almost six times greater. This was primarily due to the drop in pre-exercise session salivary IgA concentration during the fourth day of training and lack of subsequent recovery (FIG. 5).

Figure 6:
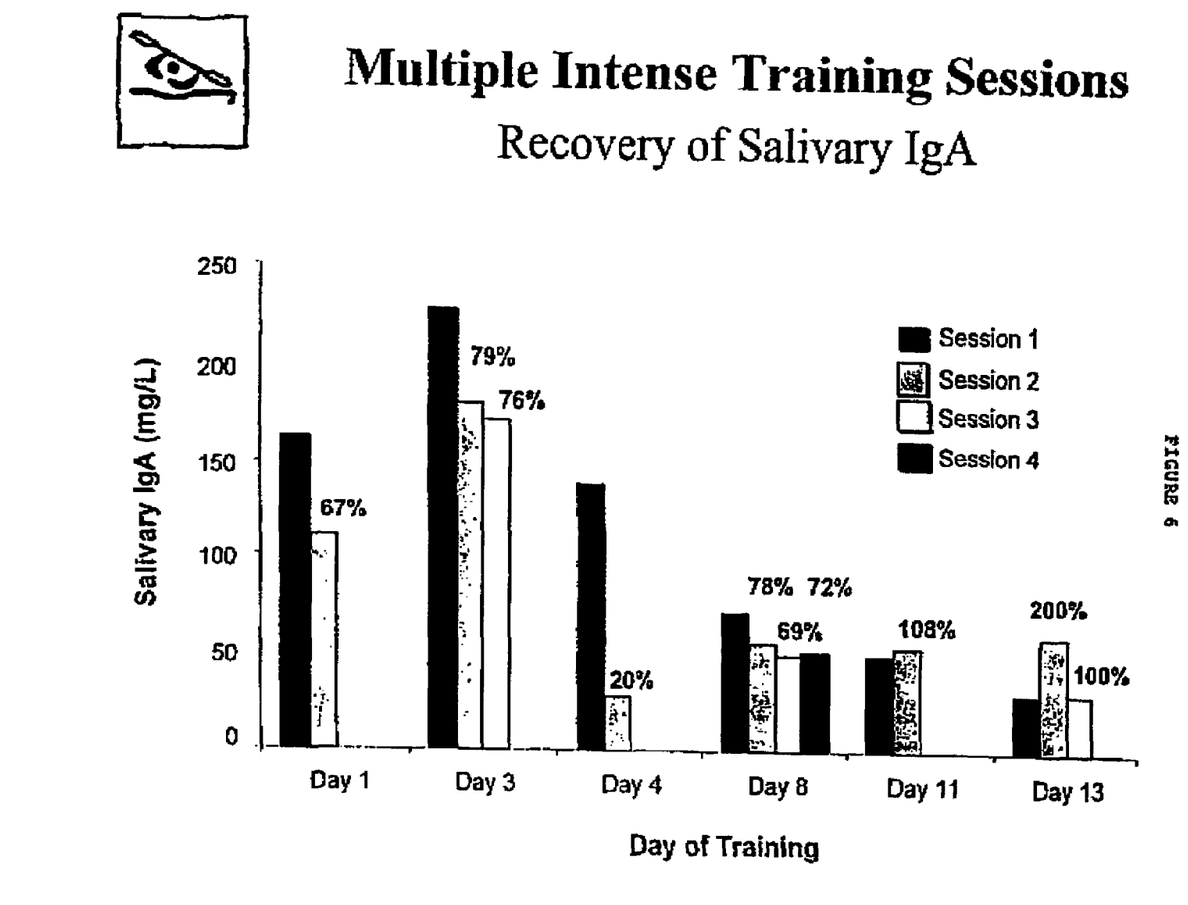
FIG. 6 The percentage recovery of pre-exercise session salivary IgA to the initial level for the day (100%), on days with multiple exercise sessions.

Multiple exercise sessions were undertaken during some of the training days. The average percent recovery of the initial IgA value for the day during the first three days was 74% (FIG. 6). On day four the recovery for the second exercise session was only 20%. Once the initial IgA concentrations fell below 50 mg/L (days 8–13) the IgA concentration showed little variation with additional training during the day (FIGS. 5 & 6).

Discussion

An adequate level of immune protection at mucosal surfaces is important for resistance against infection (23). Low levels of salivary IgA have been associated with a risk of URTI in cohorts of elite athletes (16, 26, 18, 28). Monitoring every episode of training in this case study allowed the identification of the exact exercise session that resulted in a significant suppression of the salivary IgA concentration without subsequent recovery (day 4). An important finding was the association between the early high intensity exercise with the magnitude of subsequent mucosal immune suppression, reflected by lower levels of salivary IgA after the intense exercise period.

This study highlights the benefit to the athlete and the coach if results of the salivary IgA concentration assays are available rapidly. Without the benefit of the knowledge of the mucosal immune suppression the athlete continued intensive training until restricted by a further episode of respiratory illness. In individual athletes who are prone to infection, or whose performance has declined, extensive monitoring of the athlete's training program may assist with identifying training factors that contribute to the mucosal immune suppression and potential risk of infection.

TABLE 14

The median and range, and the median session difference for the pre-training and post-training salivary immunoglobulins and albumin concentrations (mg/L) over the two week study.

| Salivary Protein | Pre-training | | Post-training | | Session Difference | | |
|---|---|---|---|---|---|---|---|
| | Median (mg/L) | Range (mg/L) | Median (mg/L) | Range (mg/L) | Median Difference (mg/L) | (95% Cl) | Significance p-value |
| IgA | 54.0 | 28–228 | 39.5 | 13–95 | 29 | 13.6–53.4 | 0.006 |
| IgG | 6.0 | 1–17 | 6.0 | 1–14 | 3 | −0.6–6.3 | 0.04 |
| IgM | 4.0 | 1–22 | 1.5 | 1–9 | 2 | 0.7–4.0 | 0.01 |
| Albumin | 56.0 | 17–184 | 36.0 | 20–89 | 15 | 6.4–34.3 | 0.003 |

Although the invention has been described with reference to specific examples it will be appreciated by those skilled in the art that the invention may be embodied in many other forms.

REFERENCES

1. Brandtzaeg P. Humoral immune response patterns of human mucosae: Induction and relation to bacterial respiratory tract infections. *J. Inf. Dis.* 1992; 165 (Suppl): S167–76.
2. Mazanec M B, Medrud J G, Kaetzel C H S and Lamm M L. A three-tiered view of the role of IgA in mucosal defence. *Immunol. Today* 1993; 14:430–435.
3. Mestecky J, Russel M W. IgA subclasses, *Mongr. Allergy* 1986; 19:277–301.
4. Delacroix D L, Dive C, Rambaud J C, Vaerman J P. IgA subclasses in various secretions and in serum. *Immunology* 1982; 47:383–385.
5. Brandtzaeg P, Kett K, Rognum T O et al. Distribution of mucosal IgA and IgG subclass-producing immunocytes and alterations in various disorders. *Mongr. Allergy* 1986; 20:179–194.
6. Kett K, Brandtzaeg P, Radl J. Haaijman J F. Different subclass distribution of IgA-producing cells in human lymphoid organs and various secretory tissues. *J. Immunol.* 1986; 136:3631–3635.
7. Muller F, Froland S S, Hvatum M, Rindl J, Brandtzaeg P. Both IgA subclasses are reduced in parotid saliva from a patient with AIDS. *Clin. Exp. Immunol.* 1991; 83:203–209.
8. Tappuni A R, Challacombe S J. A comparison of salivary immunoglobulin A (IgA) and IgA subclass concentrations in predentate and dentate children and adults. *Oral Microbial. Immunol.* 1994; 9:142–145.
9. Cannon J G. Exercise and resistance to infections. *J. Appl. Physiol.* 1993; 74:973–981.
10. Sharp C, Parry-Billings M. Can exercise damage your health? *New Scientist* 1992; 135: 33–37.
11. Brenner I K M, Shek P N, Shephard R J. Infection in athletes. *Sports Med.* 1994; 17: 86–107.
12. Heath G W, Ford E C, Craven E, Macera C A, Jackson K L, Pate R R. Exercise and the incidence of upper respiratory tract infections. *Med. Sci. Sports Exerc.* 1991; 23: 152–157.
13. Pyne D B, Gleeson M. Effects of intensive exercise training on immunity in athletes. *Int. J. Sports Med.* 1998; 19(Suppl 3): S183–S194.
14. Mackinnon L T. Immunoglobulin, antibody, and exercise. *Exer. Immunol. Rev.* 1996; 2: 1–35.
15. Gleeson M, McDonald W, Cripps A, Pyne D, Wlodarczyk J, Clancy R, Fricker P. The effect of intensive training on systemic and mucosal immunity in elite swimmers. *Clin. Exp. Immuno.* 1995; 102: 210–216.
16. Gleeson M, McDonald W A, Pyne D B, Cripps A W, Francis J L, Fricker P A, Clancy R L. Salivary IgA levels and infection risk in elite swimmers. *Med. Sci. Sports Exerc.* 1999; 31(1):67–73.
17. Mackinnon L T, Ginn E, Seymour G J. Decreased salivary immunoglobulin A secretion rate after intense interval exercise in elite kayakers. *Eur. J. Appl. Physiol.* 1993; 67: 180–184.
18. Steerenberg P A, Van Asperen I A, Van Nieuw Amerongen A, Biewenga J. Salivary levels of immunoglobulin A in triathletes. *Eur. J. Oral Sci.* 1997; 105: 305–309.
19. Hübner-Wozniak E, Sendecki W, Borkowski L. The effect of maximal 30s exercise on salivary immunoglobulin A. *Biol. Sport* 1998; 15: 61–64.
20. Gregory R L, Wallace J P, Gfell L E, Marks, J, King B A. Effect of exercise on milk immunoglobulin A. *Med. Sci. Sports Exerc.* 1997; 29:1596–1601.
21. Gleeson M, Cripps A W, Clancy R L, Husband A J, Hensley M J, Leeder S R. Ontogeny of the secretary immune system in man. *Aust. N.Z. J. Med.* 1982; 12: 255–258.
22. Shepard R J, Shek P N. Acute and chronic over-exertion: Do depressed immune responses provide useful markers? *Int. J. Sports Med.* 1998; 19: 159–171.
23. Brandtzaeg P, Beakkevold E S, Farstad I N, Jahnsen F L, Johansen F-E, Nilson E M, Yamanaka T. Regional specialisation in the mucosal immune system: what happens in the microcompartments? *Immunology Today* 1999; 20(3): 141–151.
24. Ginn E. Protocols for the physiological assessment of sprint kayak paddlers. In: *Sports specific guidelines for*

*the physiological assessment of the elite athlete.* Australian Sports Commission, 1997

25. Gleeson M, Cripps A W, Claney R L. Modifiers of the human mucosal immune system. *Immunol Cell Biol* 1995; 73: 397–404.

26. Mackinnon L T, Hooper S. Mucosal (secretory) immune system responses to exercise of varying intensity and during overtraining. *Int. J Sports Med* 1994; 15: S179–S183.

27. Sharp R L. Prescribing and evaluation interval training sets in swimming: a proposed model. *J Swim Res* 1993; 9: 36–40.

28. Thorp G D, Barnes M W. Reduction of saliva immunoglobulin levels by swim training. *Eur J Appl Physiol* 1990; 60: 61–64.

What is claimed is:

1. A method for assessing potential susceptibility to infection in a subject exposed to a stressor or stressors including:
   (a) determination of the subject's immunoglobulin A1 (IgA1) level in a sample; and
   (b) prediction of the subject's susceptibility to infection by comparison of the IgA1 level with a predetermined threshold value,
   wherein a decreased IgA1 level indicates an increased susceptibility to infection, and
   wherein an increased IgA1 level indicates a decreased susceptibility to infection.

2. A method according to claim 1 wherein the immunoglobulin level is determined in early training phase.

3. A method according to claim 1 wherein the infection is a mucosal infection.

4. A method according to claim 1 wherein the infection is a respiratory infection.

5. A method according to claim 1 wherein the threshold value is a normal population threshold value.

6. A method according to claim 1 wherein the threshold value is an internal personal threshold value.

7. A method according to claim 1 wherein the immunoglobulin is secretory immunoglobulin.

8. A method according to claim 7 wherein the secretory immunoglobulin is salivary immunoglobulin.

9. A method according to claim 8 wherein the salivary immunoglobulin is from a sample of whole unstimulated saliva.

10. A method according to claim 9 wherein the subject is not fasting when the saliva is collected.

11. A method according to claim 1 wherein the subject is an athlete.

12. A method according to claim 11 wherein the athlete is an elite swimmer.

13. A method according to claim 1 wherein the stressor is known to influence the efficacy of the immune system.

14. A method according to claim 1 wherein the subject is exposed to a physical and/or psychological stressor.

15. A method according to claim 14 wherein the physical and/or psychological stressor is long-term physical training or overtraining.

16. A method according to claim 1 wherein the immunoglobulin level is determined by radial immunodiffusion.

17. A method according to claim 1 wherein the immunoglobulin level is determined by ELISA.

18. A method according to claim 1 wherein the immunoglobulin level is determined by a rapid near-subject assay.

19. A method according to claim 1 wherein the sample is salivia, and the saliva is analysed for the immunoglobulin content in situ by contacting an assay device or system with the saliva of a subject.

20. A method according to claim 1 wherein the immunoglobulin level is determined by a self-test assay performed by the subject.

21. A method for monitoring a subject's progress following intervention therapy including:
    (a) determination of the subject's IgA1 level in a sample; and
    (b) monitoring the subject's progress by comparison of said IgA1 level with a predetermined threshold value,
    wherein a decreased IgA1 level indicates an increased susceptibility to infection, and
    wherein an increased IgA1 level indicates a decreased susceptibility to infection.

22. A method according to claim 21 wherein the IgA1 level is assessed from a sample of the subject's saliva.

23. A method for assessing potential susceptibility to respiratory infection in an elite swimmer, including:
    (a) determining the swimmer's salivary immunoglobulin A1 (IgA1) level in a sample in early training phase; and
    (b) predicting the swimmer's potential susceptibility to respiratory infection by comparison of the early training phase IgA1 level with a predetermined threshold value,
    wherein a decreased IgA1 level indicates an increased susceptibility to respiratory infection, and wherein an increased IgA1 level indicates a decreased susceptibility to respiratory infection.

24. A method according to claim 23 wherein the threshold value is a normal population threshold value.

25. A method according to claim 23 wherein the threshold value is an internal personal threshold value.

26. A method for assessing a subject's potential susceptibility to infection including:
    (a) determining the subject's immunoglobulin A1 (IgA1) level in a sample after exposure to a stressor or stressors;
    (b) allowing a recovery period
    (c) determining the subject's IgA1 level after the recovery period;
    (d) predicting the subject's potential susceptibility to infection by comparison of the IgA1 level at step (a) above with the IgA1 level at step (c) above,
    wherein a decreased IgA1 level indicates an increased susceptibility to infection, and
    wherein an increased IgA1 level indicates a decreased susceptibility to infection.

27. A method according to claim 26 wherein the infection is a mucosal infection.

28. A method according to claim 26 wherein the infection is a respiratory infection.

29. A method according to claim 26 wherein the immunoglobulin is secretory immunoglobulin.

30. A method according to claim 29 wherein the secretory immunoglobulin is salivary immunoglobulin.

31. A method according to claim 30 wherein the salivary immunoglobulin is from a sample of whole unstimulated saliva.

32. A method according to claim 31 wherein the subject is not fasting when the saliva is collected.

33. A method according to claim 26 wherein the subject is an athlete.

34. A method according to claim 33 wherein the athlete is an elite swimmer.

35. A method according to claim 26 wherein the stressor is known to influence the efficacy of the immune system.

36. A method according to claim 26 wherein the subject is exposed to a physical and/or psychological stressor.

37. A method according to claim 36 wherein the physical and/or psychological stressor is long-term physical training or overtraining.

38. A method according to claim 26 wherein the immunoglobulin level is determined by radial immunodiffusion.

39. A method according to claim 26 wherein the immunoglobulin level is determined by ELISA.

40. A method according to claim 26 wherein the immunoglobulin level is determined by a rapid near-subject assay.

41. A method according to claim 26 wherein the sample is saliva, and the saliva is analysed for the immunoglobulin content in situ by contacting an assay device or system with the saliva of a subject.

42. A method according to claim 26 wherein the immunoglobulin level is determined by a self-test assay performed by the subject.

* * * * *

UNITED STATES PATENT AND TRADEMARK OFFICE
CERTIFICATE OF CORRECTION

PATENT NO. : 6,974,674 B1
APPLICATION NO. : 09/913297
DATED : December 13, 2005
INVENTOR(S) : Clancy et al.

It is certified that error appears in the above-identified patent and that said Letters Patent is hereby corrected as shown below:

<u>Column 18,</u>
Line 2, "salivia" should be -- saliva --.

Signed and Sealed this

Twenty-seventh Day of June, 2006

JON W. DUDAS
*Director of the United States Patent and Trademark Office*